United States Patent [19]

Pittet et al.

[11] Patent Number: 4,689,428
[45] Date of Patent: * Aug. 25, 1987

[54] METHYLTHIOALKANOIC ACID ESTERS OF CITRONELLOL

[75] Inventors: Alan O. Pittet, Atlantic Highlands; Ranya Muralidhara, Fair Haven; Manfred H. Vock, Locust, all of N.J.

[73] Assignee: International Flavors & Fragrances Inc., New York, N.Y.

[*] Notice: The portion of the term of this patent subsequent to Jun. 30, 2001 has been disclaimed.

[21] Appl. No.: 901,633

[22] Filed: Aug. 29, 1986

Related U.S. Application Data

[60] Division of Ser. No. 842,206, Mar. 21, 1986, which is a continuation-in-part of Ser. No. 768,701, Aug. 23, 1985, Pat. No. 4,594,254, which is a continuation-in-part of Ser. No. 715,344, Mar. 25, 1985, Pat. No. 4,557,941.

[51] Int. Cl.$^4$ .................. C07C 149/20; A23L 1/226; A23L 1/235
[52] U.S. Cl. .................................... 560/152; 426/535
[58] Field of Search .......................... 560/152

[56] References Cited

U.S. PATENT DOCUMENTS

| | | | |
|---|---|---|---|
| 4,426,403 | 1/1984 | Cyronak et al. | 560/152 X |
| 4,521,613 | 6/1985 | Pittet et al. | 560/152 |
| 4,594,254 | 6/1986 | Pittet et al. | 560/152 X |

Primary Examiner—Michael L. Shippen
Assistant Examiner—Patricia M. Scott
Attorney, Agent, or Firm—Arthur L. Liberman

[57] ABSTRACT

Described are methylthioalkanoic acid esters of cis-3-hexenol and citronellol defined according to the structure:

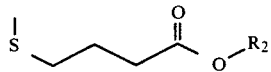

wherein $R_2$ represents cis-3-hexenyl or citronellyl and uses thereof in augmenting or enhancing the aroma or taste of foodstuffs.

2 Claims, 9 Drawing Figures

GLC PROFILE FOR FRACTION 3 OF EXAMPLE I.

GLC PROFILE FOR FRACTION 4 OF EXAMPLE I.

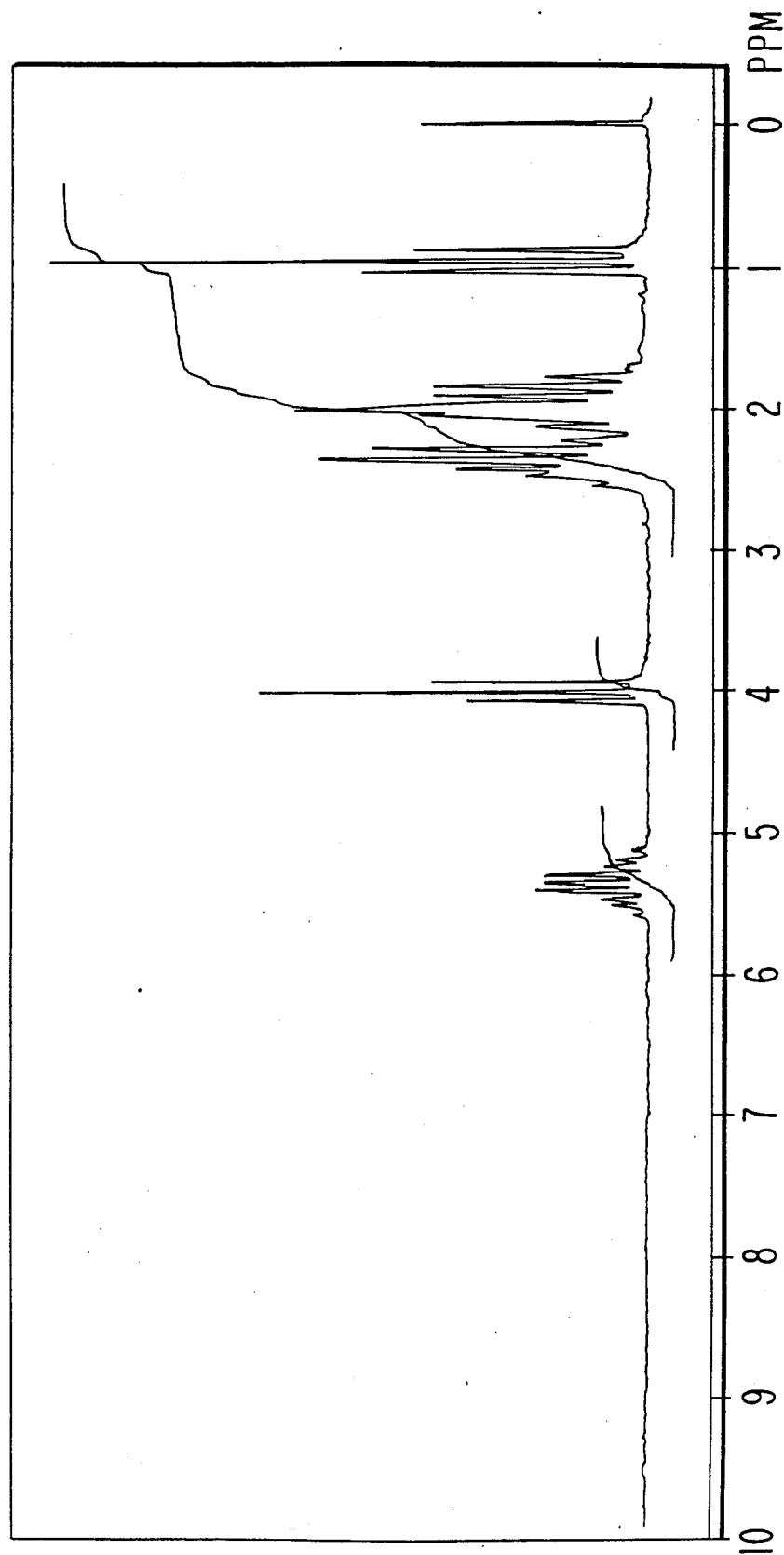

GLC PROFILE FOR FRACTION I OF EXAMPLE I.

GLC PROFILE FOR FRACTION 2 OF EXAMPLE II.

GLC PROFILE FOR FRACTION 3 OF EXAMPLE II.

GLC PROFILE FOR FRACTION 5 OF EXAMPLE II.

GLC PROFILE FOR FRACTION 5 OF EXAMPLE II.

NMR SPECTRUM FOR FRACTION 6 OF EXAMPLE I

METHYLTHIOALKANOIC ACID ESTERS OF CITRONELLOL

This application is a divisional of application for U.S. Letters Patent, Ser. No. 842,206 filed on Mar. 21, 1986, which, in turn, is a continuation-in-part of application for U.S. Letters Patent, Ser. No. 768,701 filed on Aug. 23, 1985, now U.S. Pat. No. 4,594,254 issued on June 10, 1986, which, in turn, is a continuation-in-part of application for U.S. Letters Patent, Ser. No. 715,344 filed on Mar. 25, 1985, now U.S. Pat. No. 4,557,941 issued on Dec. 10, 1985.

BACKGROUND OF THE INVENTION

This invention relates to methylthioalkanoic acid esters of cis-3-hexenol and citronellol defined according to the generic structure:

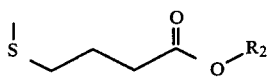

wherein $R_2$ represents cis-3-hexenyl or citronellyl and uses thereof in augmenting or enhancing the aroma or taste of foodstuffs.

Artificial flavoring agents for foodstuffs have received increasing attention in recent years. In many areas, such food flavoring agents are preferred over natural flavoring agents at least in part, because of the uniform flavor that may be so obtained. For example, natural food flavoring agents such as extracts, essences, concentrates and the like are often subject to wide variations due to changes in quality and type and treatment of the raw materials. Such variations can be reflected in the end product and results in unreliable flavor characteristics and uncertainty as to consumer acceptance and cost. Additionally, the presence of the natural product in the ultimate food may be undesirable because of the increased tendency to spoil. This is particularly troublesome in convenience and snack food usage where such products as dips, soups, chips, prepared dinners, canned foods, sauces, gravies and the like are apt to be stored by the consumer for some time prior to use.

The fundamental problem in preparing artificial flavoring agents is that of achieving as nearly as possible a true flavor reproduction. This generally proves to be a difficult task since the mechanism for flavoring development in many foods is not understood. This is notable in products having green, spicy, licorice, fresh lemon, lemon juice-like and grapefruit aroma and taste nuances.

Reproduction of green, spicy, licorice, fresh lemon, lemon juice-like, floral and grapefruit aroma and taste nuances has been the subject of long and continuous searches by those engaged in the production of foodstuffs. The severe shortage of food in many parts of the world has given rise to the need for utilizing non-meat sources of proteins and making such proteins as palatable as possible. Hence, materials which will closely simulate or exactly reproduce the flavor and aroma of natural products such as fruit, grapefruit, tropical fruit and mango flavored foodstuffs are required.

Foof flavors in the thioalkanoic acid ester are kown in the prior art.

Thus, U.S. Pat. No. 4,426,403 discloses the genus of compounds defined according to the structure:

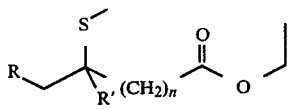

wherein R and R' represent hydrogen or $C_1$–$C_3$ alkyl as food flavorants, particularly in the fruity, vegetable or green pine needle aroma and taste area.

U.S. Pat. No. 3,870,800 relates to the processes for augmenting or enhancing the aroma or taste of foodstuffs using methylthio butanoic acid derivatives. U.S. Pat. No. 3,904,556, at Example XVII thereof states that ethyl-4-(methylthio)butyrate may be added to a cheese sauce to increase the notes usually present in the surface ripened cheese and to increase the cheese flavor intensity. In Example XX it is further stated that this compound, ethyl-4-(methylthio)butyrate is added to tobacco to enhance the pineapple character of a fruit flavor for tobacco.

U.S. Pat. No. 3,879,562 issued on Apr. 22, 1975 and the reissue patent thereof, U.S. Pat. No. Re. 30,370 issued on Aug. 12, 1980 disclose the genus of compounds having the structure:

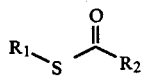

wherein $R_1$ represents alkyl, cycloalkyl, aryl, aralkyl, alkaryl, or alkenyl and $R_2$ represents alkyl, alkyl thioalkyl, aralkyl, alkaryl, or aryl in augmenting or enhancing the aroma or taste of various foodstuffs.

McFadden, et al, Analytical Chemistry 37,560, have suggested the presence of methyl thiohexanoate and thioheptanoate in oil derived from hops, and Buttery, et al, have reported similar work in J. Chromatography 18,399. Schultz, Dav and Libbey, "The Chemistry and Physiology of Flavors", Westport, Conn.: Avi. Publishing Co. 1967, at page 412 disclose thioesters useful in flavoring.

Nevertheless, nothing in the prior art discloses the methylthioalkanoic acid esters of cis-3-hexenol and citronellol of our invention or their unexpected, unobvious and advantageous uses in augmenting or enhancing the aroma or taste of foodstuffs.

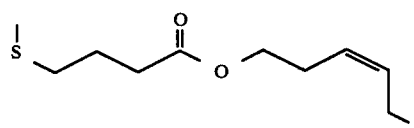

(Conditions: 8'×0.125" SE-30 column programmed at 220° C. isothermal).

Figure 2:
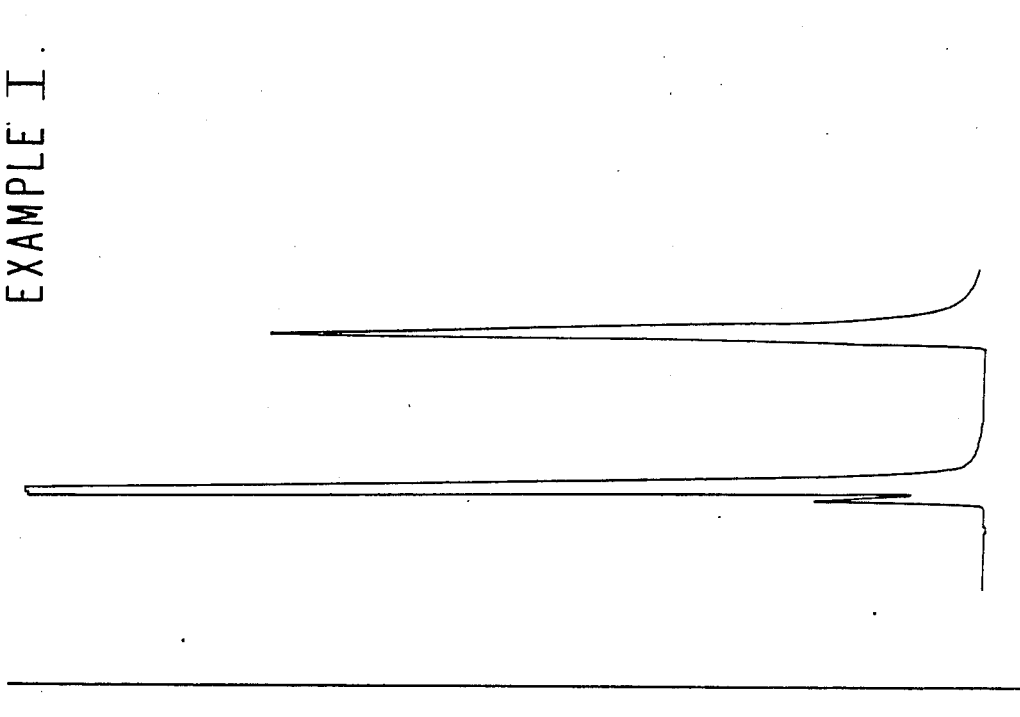

FIG. 2 is the GLC profile for fraction 3 of the distillation product of the reaction product of Example I containing the compound having the structure:

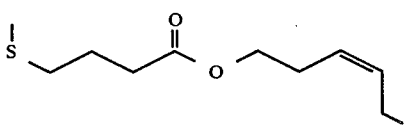

(Conditions: 8'×0.125" SE-30 column programmed at 220° C. isothermal).

FIG. 3 is the NMR spectrum for fraction 4 of the distillation product of the reaction product of Example I containing the compound having the structure:

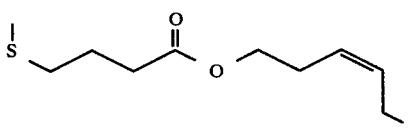

(Conditions: Field strength: 100 MHz; solvent: $CFCl_3$).

Figure 4:
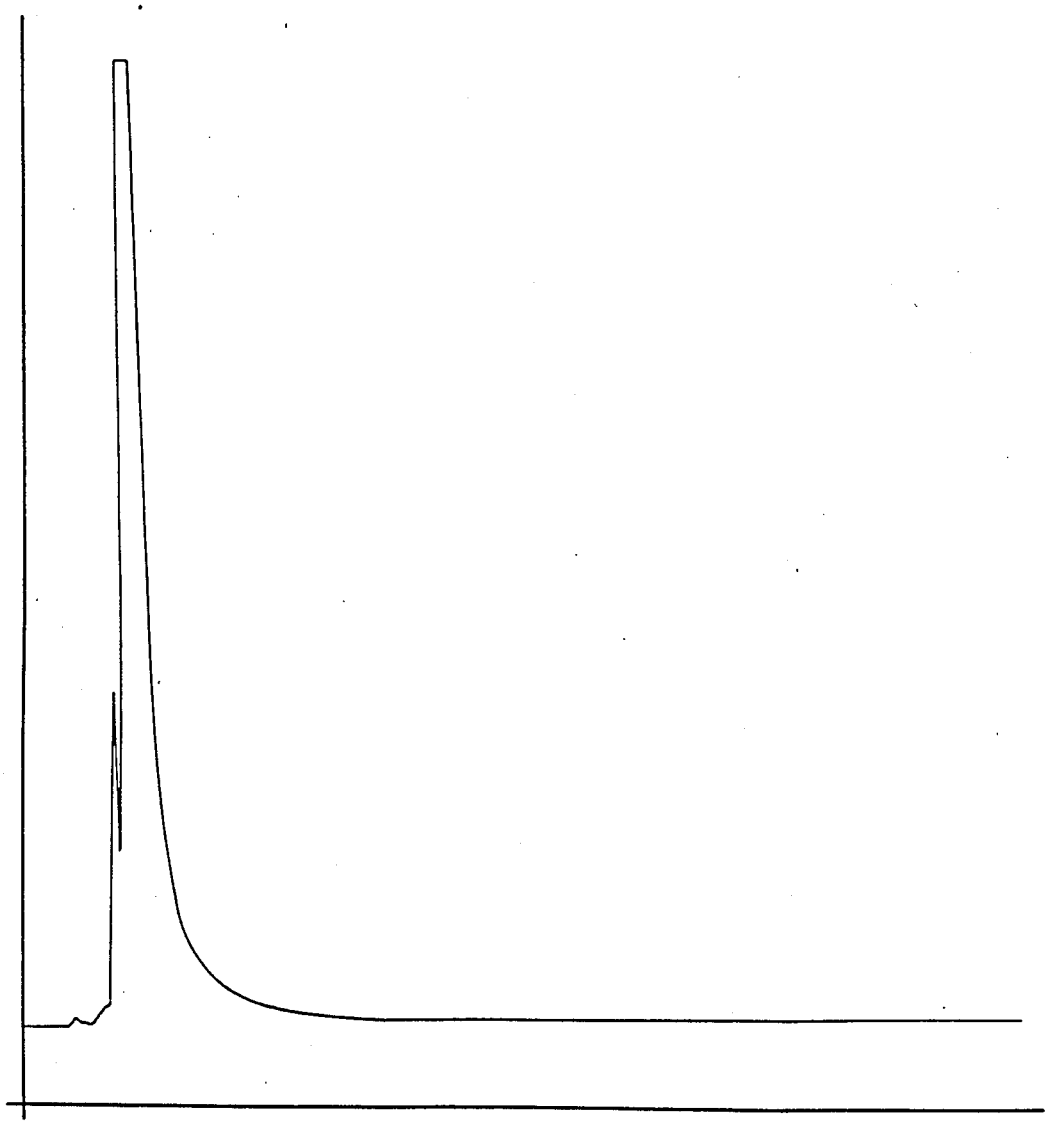

FIG. 4 is the GLC profile for fraction 1 of the distillation product of the reaction product of Example II containing a mixture of compounds having the structures:

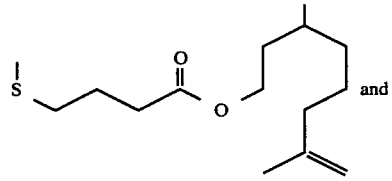

(mole ratio of compound having the structure:

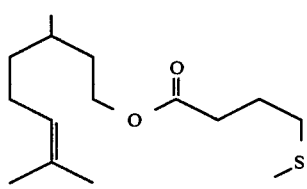

to compound having the structure:

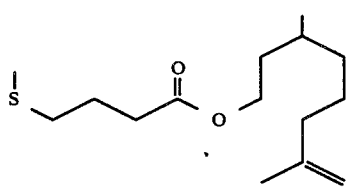

being 85:15).

Figure 5:
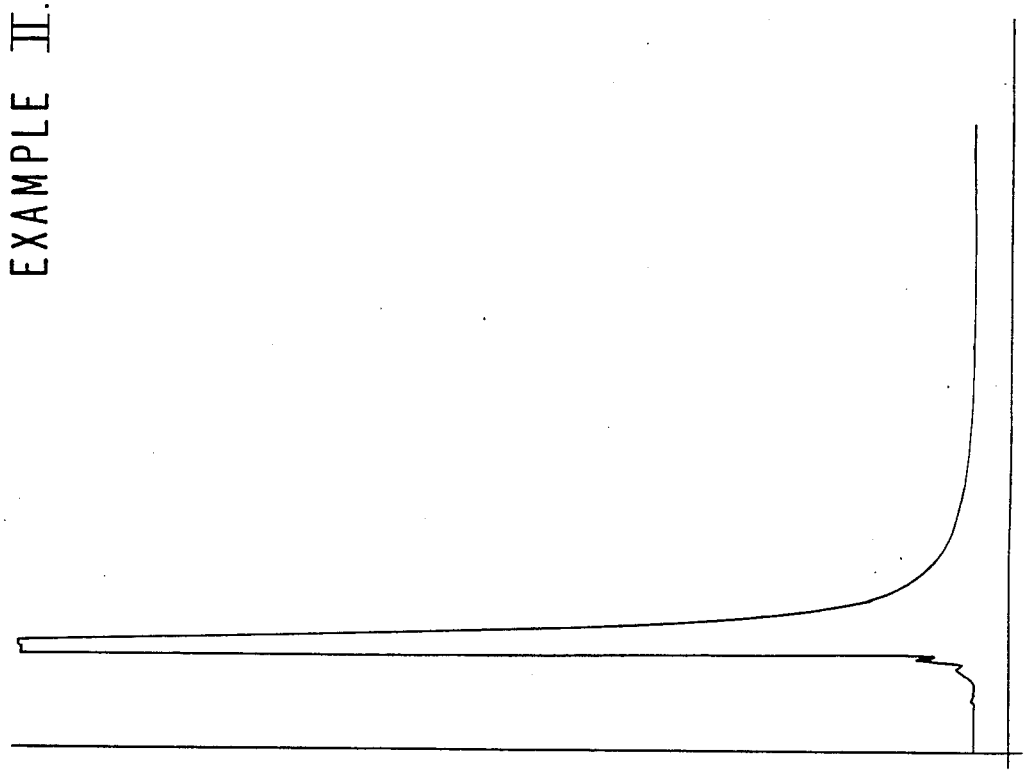

FIG. 5 is the GLC profile for fraction 2 of the distillation product of the reaction product of Example II containing a mixture of compounds having the structures:

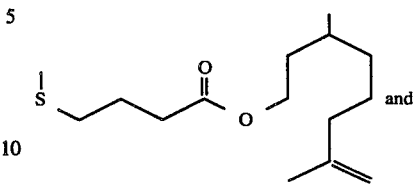

(mole ratio of compound having the structure:

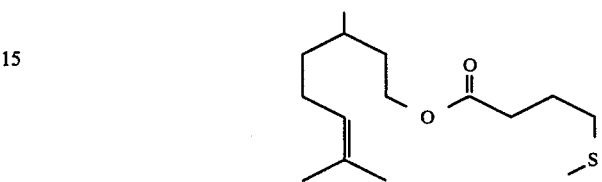

to compound having the structure:

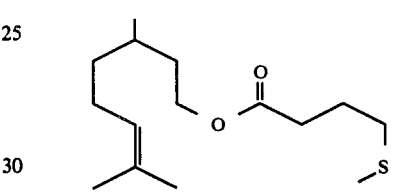

being 85:15).

Figure 6:
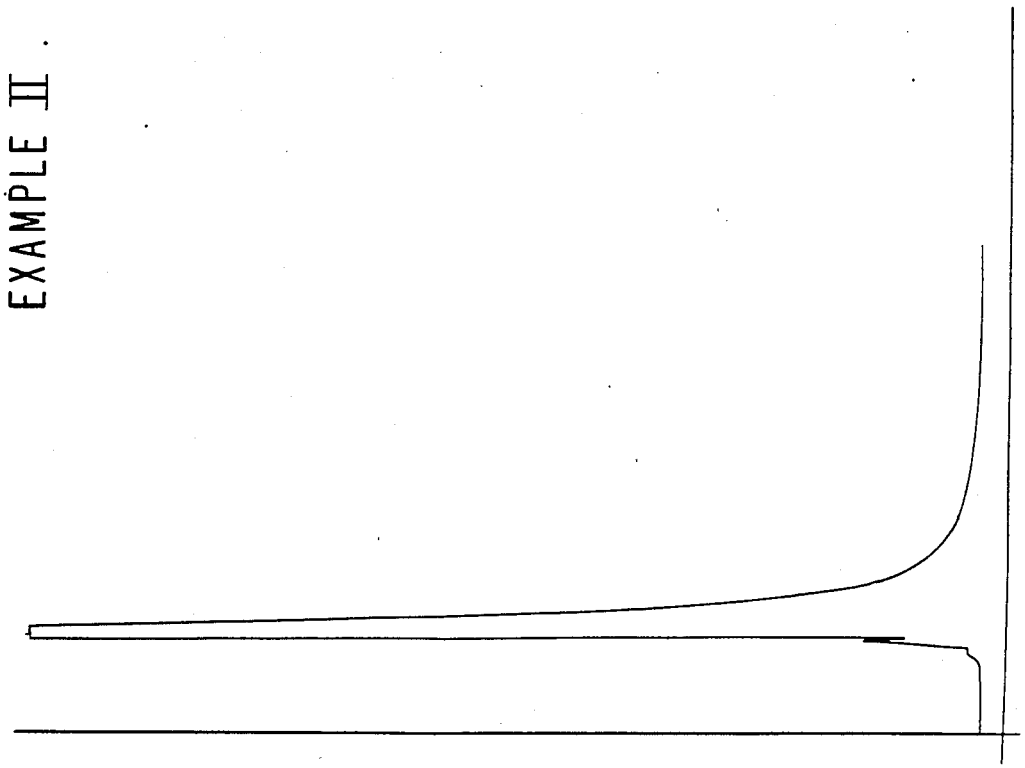

FIG. 6 is the GLC profile for fraction 3 of the distillation product of the reaction product of Example II containing a mixture of compounds having the structures:

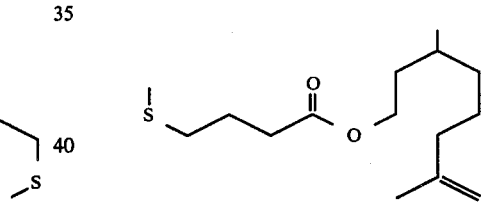

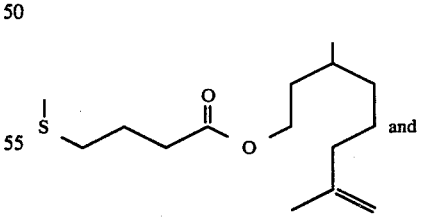

(mole ratio of compound having the structure:

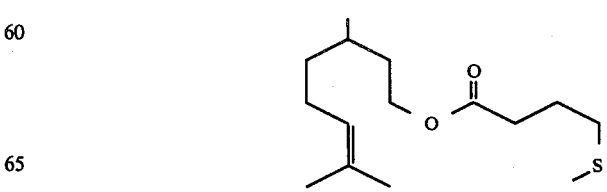

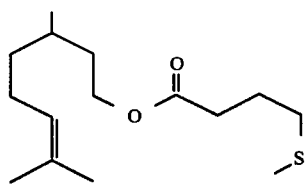

to compound having the structure:

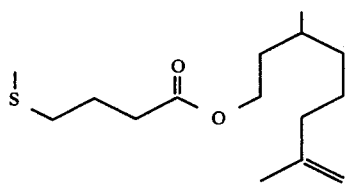

being 85:15).

Figure 7:
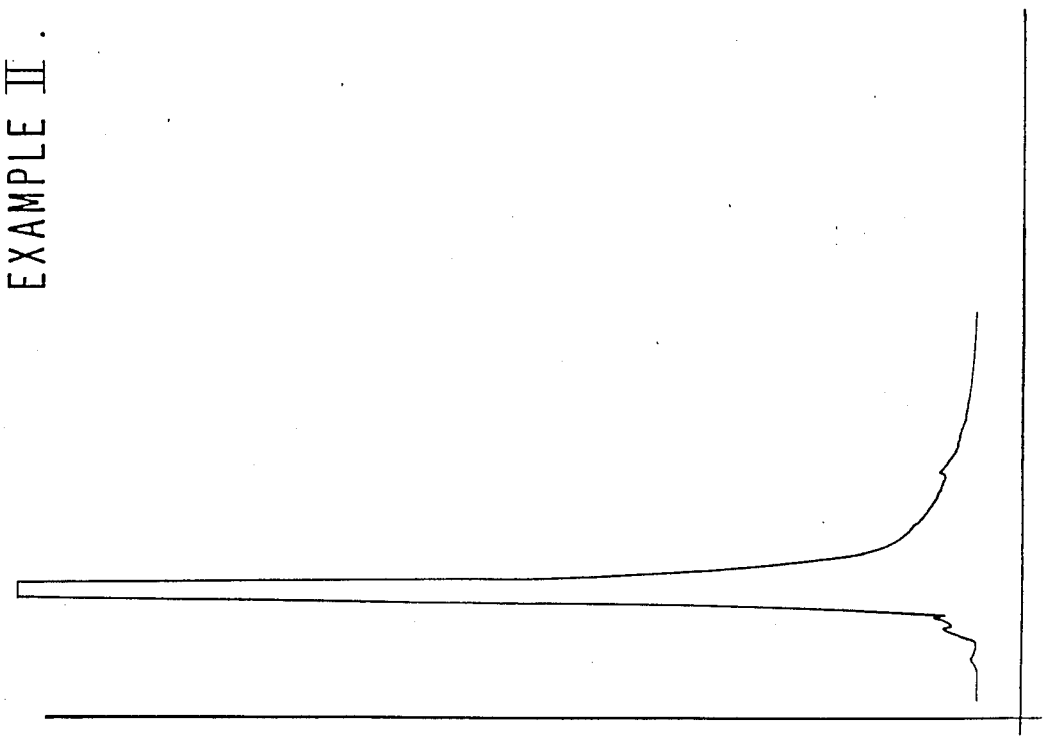

FIG. 7 is the GLC profile for fraction 5 of the distillation product of the reaction product of Example II containing a mixture of compounds having the structures:

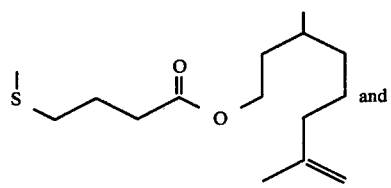

(mole ratio of compound having the structure:

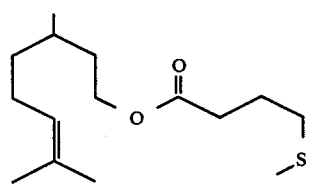

to compound having the structure:

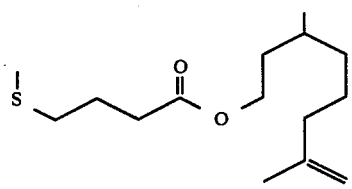

being 85:15).

Figure 8:
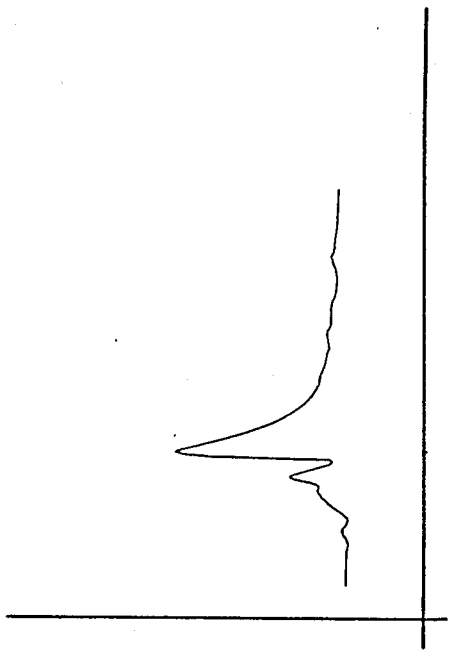

FIG. 8 is the GLC profile for fraction 6 of the distillation product of the reaction product of Example II containing a mixture of compounds having the structures:

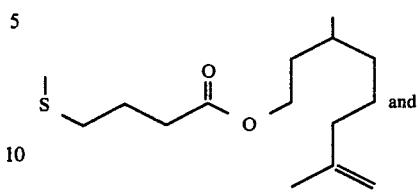

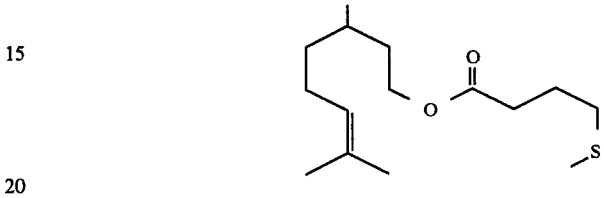

(mole ratio of compound having the structure:

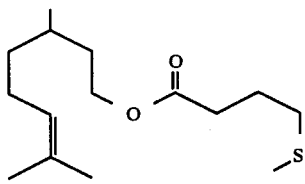

to compound having the structure:

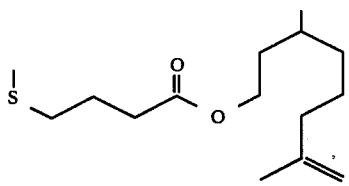

being 85:15).

Figure 9:
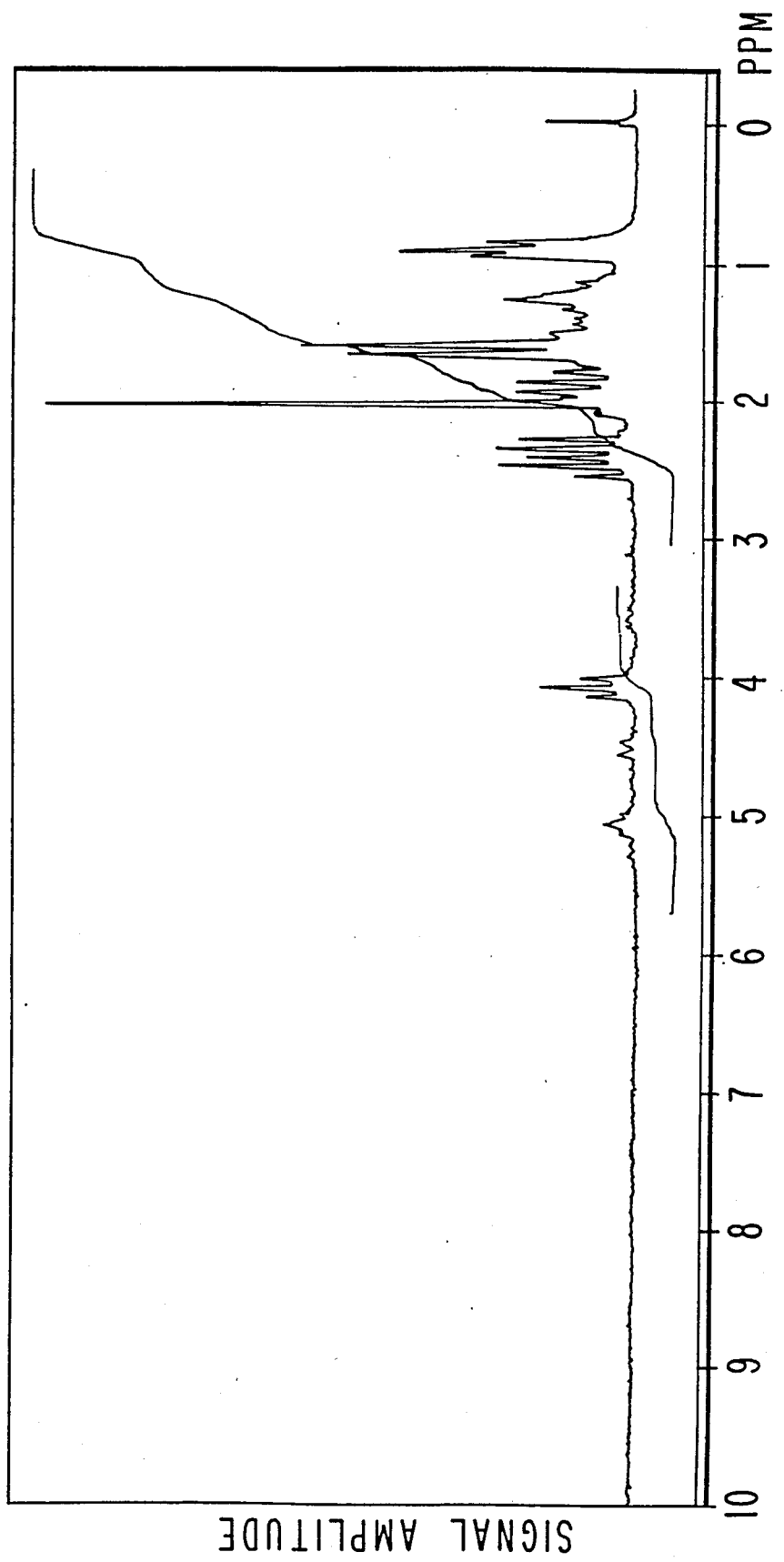

FIG. 9 is the NMR spectrum for fraction 6 of the distillation product of the reaction product of Example II containing a mixture of compounds having the structures:

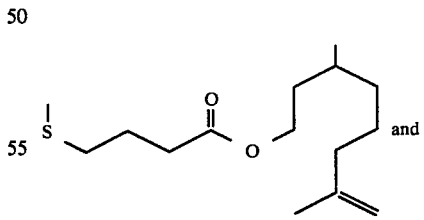

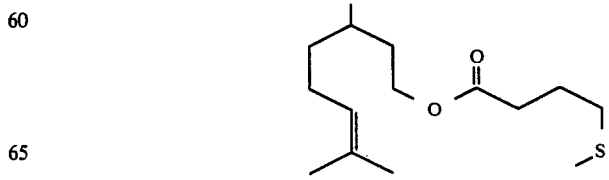

(mole ratio of compound having the structure:

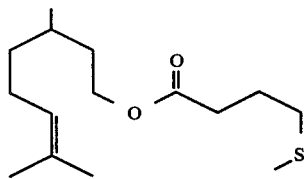

to compound having the structure:

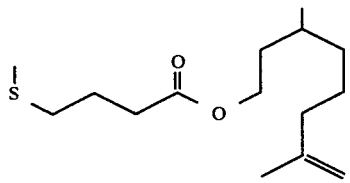

being 85:15) (Conditions: Field strength: 100 MHz; solvent: $CFCl_3$).

THE INVENTION

The present invention provides methylthioalkanoic acid esters of cis-3-hexenol and citronellol useful for augmenting or enhancing the aroma or taste of foodstuffs, said methylthioalkanoic acid esters of cis-3-hexenol and citronellols being defined according to the generic structure:

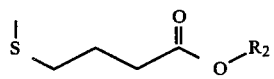

wherein $R_2$ represents citronellyl or cis-3-hexenyl as well as methods for augmenting or enhancing or modifying the organoleptic properties, e.g., taste and aroma of said foodstuffs.

The methylthioalkanoic acid esters of cis-3-hexenol and citronellol of our invention augment or enhance green, spicy, licorice, fresh lemon, lemon juice-like, floral and grapefruit aroma and taste nuances making them useful for augmenting or enhancing flavors for such foodstuffs as fruit, grapefruit, tropical fruit and mango flavored foodstuffs.

The methylthioalkanoic acid esters of cis-3-hexenol and citronellol of our invention may be prepared by reacting an ester having the structure:

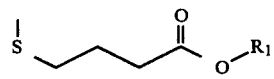

wherein $R_1$ represents $C_1$-$C_3$ alkyl with an alcohol having the formula:

$R_2$—OH which may be cis-3-hexenol having the structure:

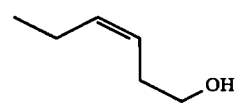

or citronellol which is a mixture of compounds having the structures:

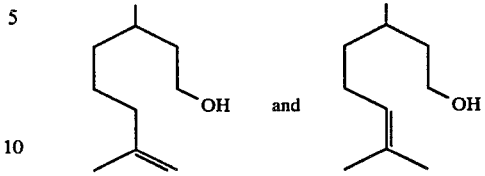

(with the mole ratio of compound having the structure:

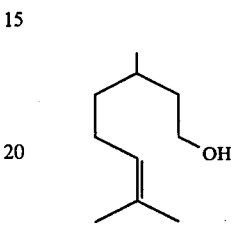

to compound having the structure:

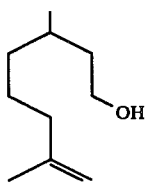

being in the range of from about 70:30 up to about 90:10; and the preferred mole ratio being about 85:15) in the presence of a metal alkoxide defined according to the formula:

M—(OR$_3$)$_N$ wherein M represents alkali metal such as sodium potassium or lithium and $R_3$ represents lower alkyl such as methyl, ethyl, n-propyl, isopropyl or t-butyl or M represents aluminum and $R_3$ represents isopropyl and wherein N is 1 when M is alkali metal and N is 3 where M is aluminum; and wherein $R_2$ represents citronellyl or cis-3-hexenyl.

The reaction is carried out at temperatures of from about 10° C. up to about to about 110° C. (e.g., reflux conditions) under a nitrogen atmosphere. The mole ratio of compound having the structure:

to compound having the formula:

$R_2$—OH may vary from about 2:1 up to about 1:2 with a mole ratio of about 1:1 being preferred. The catalyst for the reaction having the formula:

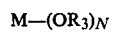

M—(OR$_3$)$_N$ is preferably admixed with the reaction mass prior to heating and stirring the reaction mass and is preferably in the form of a methanolic solution of between about 15% and about 40%.

The reaction for preparing the methylthioalkanoic acid esters of cis-3-hexenol and citronellol of our invention is shown thusly:

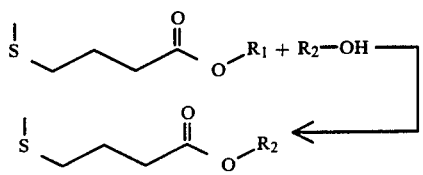

The time of reaction may vary from about 0.25 hours up to about 5 hours.

Times of reaction are dependent upon the temperature of reaction.

At the end of the reaction the reaction mass is cooled to room temperature (if in the first place it is heated) and admixed with a solvent which is inert to the reactant such as methylene dichloride. The resulting product is washed with water and then dried and distilled, preferably by means of fractional distillation. The various fractions are selected for their organoleptic properties.

Examples of the products of our invention and their organoleptic properties are as follows:

TABLE I

| STRUCTURE OF COMPOUND(S) | ORGANOLEPTIC PROPERTIES |
|---|---|
| Compound having the structure:<br>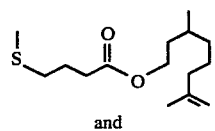<br>prepared according to Example I | A green, spicy and licorice Aroma and taste profile at 3 ppm causing it to be useful in fruit flavors. |
| Mixture of compounds having the structures:<br>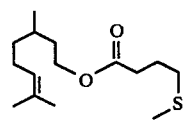<br>and<br>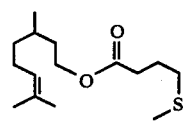<br>prepared according to Example II (mole ratio of compound having the structure:<br>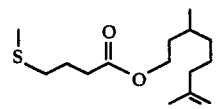 | A fresh lemon, lemon, juice-like, floral and grapefruit aroma and taste profile at 2 ppm causing it to be useful in mango, grapefruit and tropical fruit flavored foodstuffs. |

TABLE I-continued

| STRUCTURE OF COMPOUND(S) | ORGANOLEPTIC PROPERTIES |
|---|---|
| being 85:15). | |

It should be noted that in the practice of our invention the mole ratio of compound having the structure:

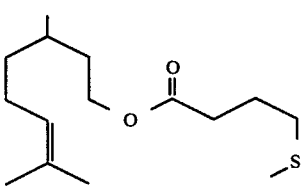

to compound having the structure:

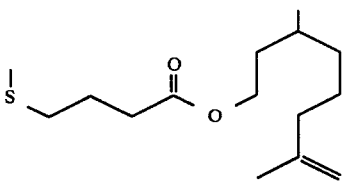

in the mixture of compounds having the structures:

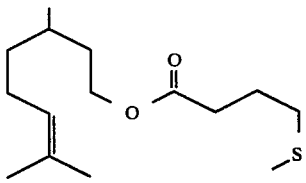

and

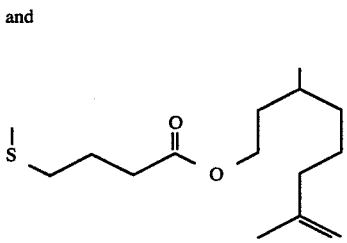

may vary from about 70:30 up to about 90:10 as a result of the precursor of this reaction product being citrinellol which is a mixture of compounds having the structures:

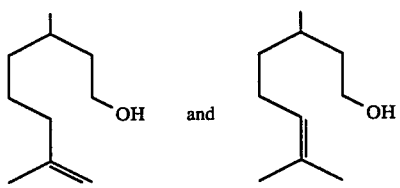

wherein the mole ratio of compound having the structure:

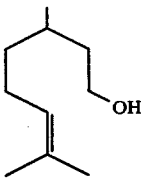

to compound having the structure:

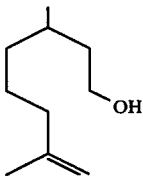

is in the range of from about 70:30 up to about 90:10 as stated, supra.

Thus, the methylthioalkanoic acid esters of cis-3-hexenol and citronellol of our invention can be used to alter, vary, fortify, modify, enhance or otherwise improve the organoleptic properties including flavor and/or aroma of a wide variety of materials which are ingested, consumed or otherwise organoleptically sensed.

The term "alter" in its various forms will be understood herein to mean the supplying or imparting of a flavor character or note to an otherwise bland, relatively tasteless substance or augmenting an existing flavor characteristic where the natural flavor is deficient in some regard or supplmenting the existing flavor or aroma impression to modify the organoleptic character. The materials which are so altered are generally referred to herein as consumable materials.

Such methylthioalkanoic acid esters of cis-3-hexenol and citronellol of our invention are accordingly useful in flavoring compositions. Flavoring compositions are herein taken to mean those which contribute a part of the overall flavor impression by supplmenting or fortifying a natural or artificial flavor in a material, as well as those which supply substantially all the flavor and/or aroma character to a consumable article.

The term "foodstuff" as used herein includes both solid and liquid ingestible materials for man or animals, which materials usually do, but need not, have nutritional value. Thus, foodstuffs includes meats, gravies, soups, convenience foods, malt and other alcoholic or non-alcoholic beverages, milk and dairy products, nut butters such as peanut butter and other spreads, seafoods including fish, crustaceans, mollusks and the like, candies, breakfast foods, baked goods, vegetables, cereals, soft drinks, snack foods, dog and cat foods, other veterinary products, and the like.

When the methylthioalkanoic acid esters of cis-3-hexenol and citronellol of this invention are used in food flavoring compositions, they can be combined with conventional flavoring materials or adjuvants. Such co-ingredients or flavoring adjuvants are well known in the art for such use and have been extensively described in the literature. Apart from the requirement that any such adjuvant material is ingestibly acceptable, and thus non-toxic or otherwise non-deleterious, conventional materials can be used and broadly include other flavor materials, vehicles, stabilizers, thickeners, surface active agents, conditioners and flavor intensifiers.

Examples of preferred co-flavoring adjuvants are:
Methyl thiazole alcohol (4-methyl-5- -hydroxyethyl thiazole);
2-Methyl butanethiol;
4-Mercapto-2-butanone;
3-Mercapto-2-pentanone;
1-Mercapto-2-propanone;
Benzaldehyde;
Furfuryl alcohol;
2-Mercapto propionic acid;
Alkyl pyrazine;
Methyl pyrazine;
2-Ethyl-3-methyl pyrazine;
Tetramethyl pyrazine;
Polysulfides;
Dipropyl disulfide;
Methyl benzyl disulfide;
Alkyl thiophenes;
2-Butyl thiophene;
2,3-Dimethyl thiophene;
5-Methyl furfural;
Acetyl furan;
2,4-Decadienal;
Guiacol;
Phenyl acetaldehyde;
δ-Decalactone;
d-Limonene;
Acetoin;
Amyl acetate;
Maltol;
Ethyl butyrate;
Levulinic acid;
Piperonal;
Ethyl acetate;
n-Octanal;
n-Pentanal;
Hexanal;
Diacetyl;
Monosodium glutamate;
Monopotassium glutamate;
Sulphur-containing amino acids, e.g., cysteine;
Hydrolyzed vegetable protein;
2-Methylfuran-3-thiol;
2-Methyldihydrofuran-3-thiol;
2,5-Dimethylfuran-3-thiol;
Hydrolyzed fish protein;
Nor-methyl jasmonate (described in U.S. Pat. No. 4,294,863 issued on Oct. 13, 1981);
Dihydro-nor-methyl jasmonate (described in U.S. Pat. No. 4,294,863 issued on Oct. 13, 1981);
2-Methyl-4-n-propyl-1,3-oxathiane;
2-Methyl-6-n-propyl-1,3-oxathiane;
Guava extract;
Mango extract;
Vanillin;
Phenyl acetaldehyde;
Benzyl acetate;
Benzyl alcohol;
Ethyl-3-methyl-3-phenyl-glycidate;
Heliotropin;
Furfural;
Ocimene;
Linalool;
Cis-allocimene;
Trans-allocimene;
Myrcene;

Gamma-hexalactone; and
Gamma-heptalactone.

The methylthioalkanoic acid esters of cis-3-hexenol and citronellol or the compositions incorporating them, as mentioned above, can be combined with one or more vehicles or carriers for adding them to the particular product to be flavored. Vehicles can be edible or otherwise suitable materials such as ethyl alcohol, propylene glycol, water and the like. Carriers include materials such as gum arabic, carrageenan, guar gum, xanthan gum and the like. The methylthioalkanoic acid esters of cis-3-hexenol and citronellol of our invention can be incorporated with the carriers by conventional means such as spray-drying, drum-drying and the like. Such carriers can also include materials for coacervating the methylthioalkanoic acid esters of cis-3-hexenol and citronellol of our invention (and other flavoring ingredients, as present) to provide encapsulated products. When the carrier is an emulsion, the flavoring composition can also contain emulsifiers such as mono- and diglycerides or fatty acids and the like. With these carriers or vehicles, the desired physical form of the composition can be prepared.

The quantity of methylthioalkanoic acid esters of cis-3-hexenol and citronellol utilized should be sufficient to impart the desired flavor characteristic to the product, but on the other hand, the use of an excessive amount of the derivative is not only wasteful and uneconomical, but in some instances too large of a quantity may unbalance the flavor or other organoleptic properties of the product consumed. The quantity used will vary depending upon the ultimate foodstuff; the amount and type of flavor initially present in the foodstuff; the further process or treatment steps to which the foodstuff will be subjected; regional and other preference factors; the type of storage, if any, to which the product will be subjected; and the preconsumption treatment, such as baking, frying and so on, given to the product by the ultimate consumer. Accordingly, the terminology "effective amount" and "sufficient amount" is understood in the context of the present invention to be quantitatively adequate to alter the flavor of the foodstuff.

It is accordingly preferred that the ultimate composition contain from about 0.001 parts per million (ppm) to about 250 ppm of methylthioalkanoic acid esters of cis-3-hexenol and citronellol thereof. More particularly, in food compositions it is desirable to use from about 0.001 ppm to 100 ppm for enhancing flavors and in certain preferred embodiments of the invention, from abourt 0.001 to 50 ppm of the derivatives are included to add positive flavors to the finished product.

The amount of methylthioalkanoic acid esters of cis-3-hexenol and citronellol thereof of our invention to be utilized in flavoring compositions can be varied over a wide range depending upon the particular quality to be added to the foodstuff. Thus, amounts of one or more derivatives according to the present invention of from about 0.04 ppm up to 80 or 90 percent of the total flavoring composition can be incorporated in such compositions. It is generally found to be desirable to include from about 0.05 ppm up to about 0.1 percent of the methylthioalkanoic acid esters of cis-3-hexenol and citronellol in such compositions.

The following examples are given to illustrate embodiments of the invention as it is preferred to practice it. It will be understood that these examples are illustrative and the invention is not to be considered as restricted thereto except as indicated in the appended claims.

All parts, proportions, percentages and ratios used herein are by weight unless otherwise indicated.

EXAMPLE I

Preparation of the cis-3-hexenyl ester of 4-(methylthio)butyric acid

Reaction:

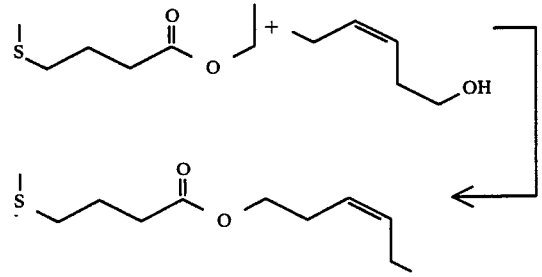

Into a 50 cc reaction vessel equipped with stirrer and reflux condenser are placed a mixture of 10.0 grams of cis-3-hexenol; 8.1 grams of the compound having the structure:

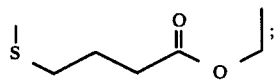

and 0.5 grams of a 25% methanol solution of sodium methoxide.

The resulting reaction mixture is stirred for a period of 0.25 hours whereupon it is transferred to a separatory funnel and washed with 100 ml water. The organic phase is separated and distilled in a micro distillation apparatus yielding the following fractions:

| Fraction No. | Vapor Temp (°C.) | Liquid Temp. (°C.) | Vacuum mm/Hg. Presssure | Weight of Fraction |
|---|---|---|---|---|
| 1 | 53/53 | 98/63 | 5.0 | 4.7 |
| 2 | 110 | 135 | 5.0 | 1.0 |
| 3 | 140 | 137 | 5.0 | 3.1 |
| 4 | 135 | 145 | 4.0 | 4.0 |

Fraction 4 of the foregoing distillation has a green, spicy and licorice aroma and taste profile at 3 ppm causing it to be useful in fruit flavors.

The resulting product has the structure:

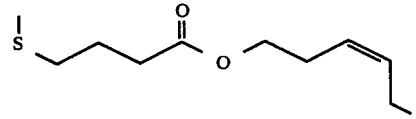

as confirmed by NMR, GLC, IR and mass spectral analyses.

Figure 1:
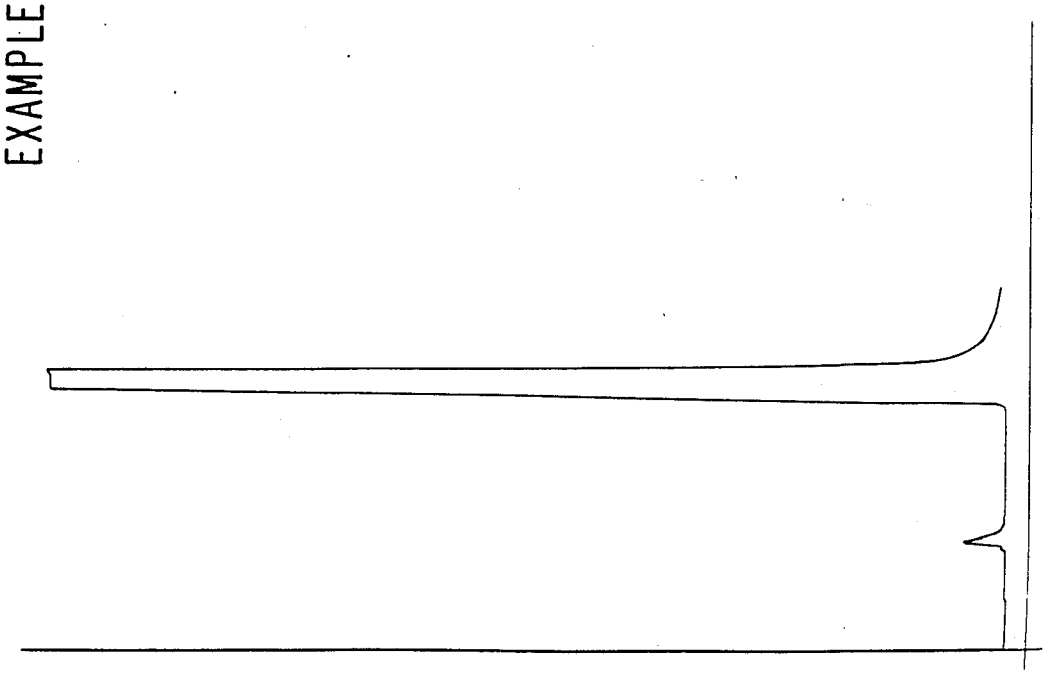
FIG. 1 is the GLC profile for fraction 4 of the distillation product of the reaction product of Example I containing the compound having the structure.

FIG. 1 is the GLC profile for fraction 4 of the foregoing distillation containing the compound having the structure:

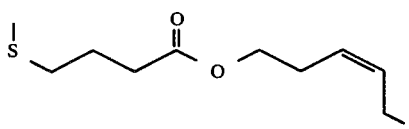

(Conditions: 8'×0.125" SE-30 column programmed at 220° C. isothermal).

FIG. 2 is the GLC profile for fraction 3 of the foregoing distillation (Conditions: 8'×0.125" SE-30 column programmed at 220° C. isothermal).

FIG. 3 is the NMR spectrum for the compound having the structure:

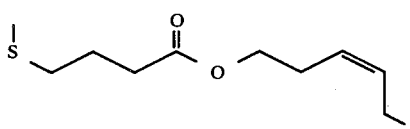

(fraction 4) (Conditions: Field strength: 100 MHz; solvent: CFCl₃).

EXAMPLE II

Preparation of citronellyl-4-(methylthio)butyrate

Reactions:

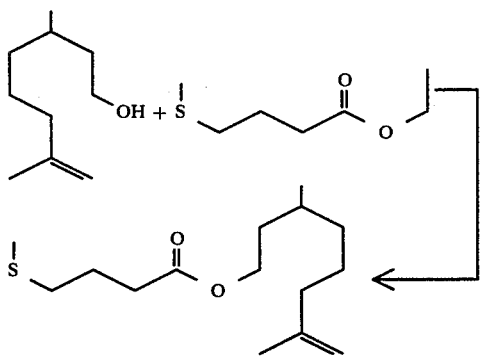

and

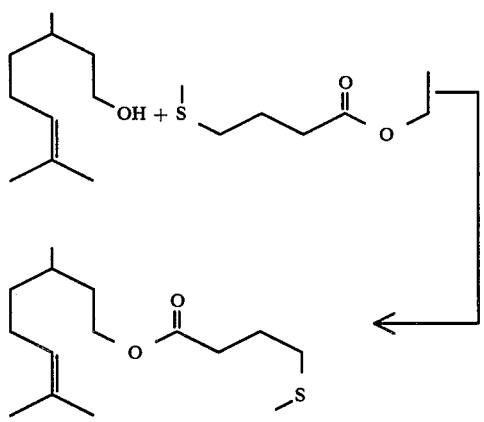

Into a 250 ml reaction vessel equipped with stirrer, thermometer, nitrogen blanket apparatus, heating mantle and reflux condenser is placed 15.6 grams citronellol (a mixture of compounds having the structures:

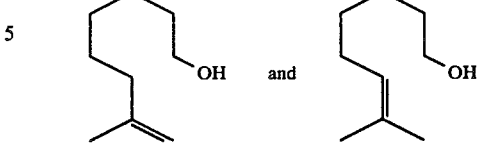

with a mole ratio of the compound having the structure:

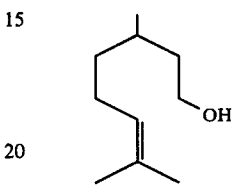

to the compound having the structure:

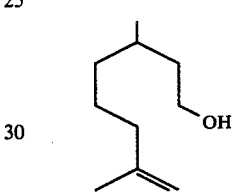

being 85:15); 8.1 grams of ethyl(4-methylthio)butyrate having the structure:

and 0.5 grams of a 25% solution of sodium methoxide in methanol.

With stirring, the reaction mass is heated to 100° C. and maintained at 100° C. (reflux) for a period of 0.25 hours. At the end of the 0.25 hour period the reaction mass is cooled to room temperature and the cooled reaction mass is admixed with 50 ml methylene chloride and then washed with two 50 ml portions of water. The reaction mass is then dried over anhydrous sodium sulfate and distilled on a micro distillation apparatus yielding the following fractions:

| Fraction No. | Vapor Temp. (°C.) | Liquid Temp. (°C.) | Vacuum mm/Hg. Pressure | Weight of Fraction |
|---|---|---|---|---|
| 1 | 98/90 | 110/110 | 13.0 | 4.1 |
| 2 | 98 | 118 | 10.0 | 3.4 |
| 3 | 90 | 135 | 10.0 | 3.5 |
| 4 | 93 | 190 | 10.0 | 2.5 |
| 5 | 90 | 205 | 10.0 | 0.4 |
| 6 | 166 | 220 | 10.0 | 2.9 |

The resulting product is a mixture of compounds having the structures:

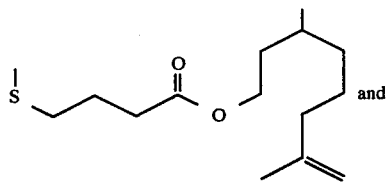

and

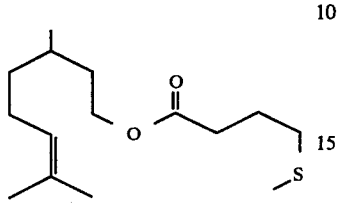

(with the mole ratio of the compound having the structure:

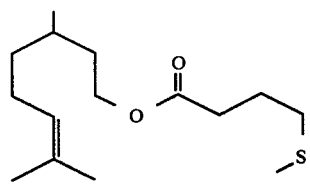

to the compound having the structure:

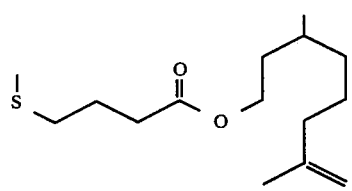

being 85:15).

Thus, a majority of the reaction mass is the compound having the structure:

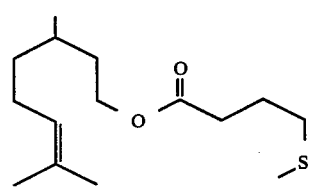

and this is confirmed by NMR, mass spectral, IR and GLC analyses.

Fraction 6 of the foregoing distillation product contains a mixture of the compounds having the structures:

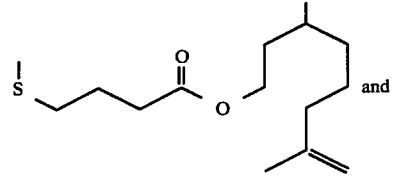

and

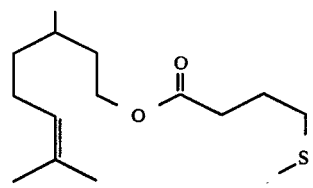

and this mixture has a fresh lemon, lemon juice-like, floral and grapefruit aroma and taste profile at 2 ppm causing the mixture of compounds having the structures:

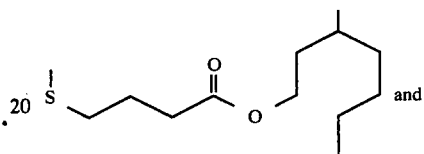

and

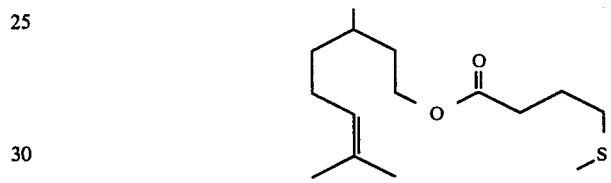

to be useful in mango, grapefruit and tropical fruit flavored foodstuffs.

FIG. 4 is the GLC profile for fraction 1 of the foregoing distillation containing the compounds having the structures:

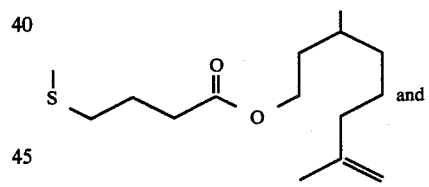

and

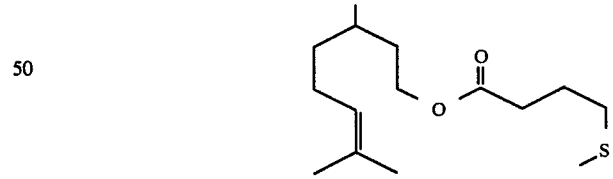

(with the mole ratio of the compound having the structure:

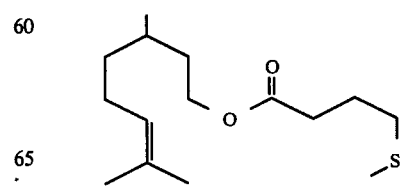

to compound having the structure:

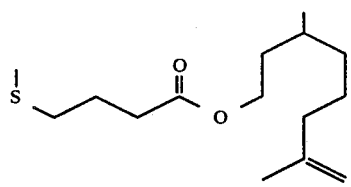

being 85:15) (Conditions: SE-30 column programmed at 220° C. isothermal).

FIG. 5 is the GLC profile for fraction 2 of the foregoing distillation containing the compounds having the structures:

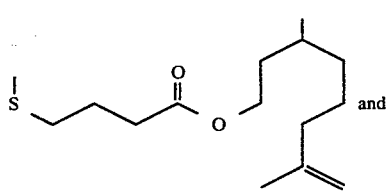 and

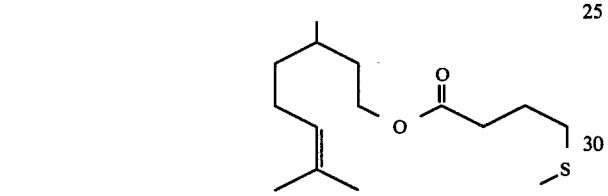

(with the mole ratio of the compound having the structure:

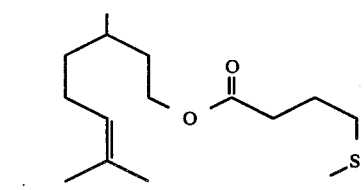

to compound having the structure:

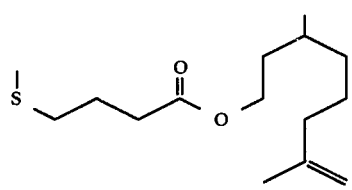

being 85:15).

FIG. 6 is the GLC profile for fraction 3 of the foregoing distillation containing a mixture of compounds having the structures:

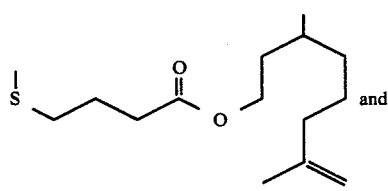 and

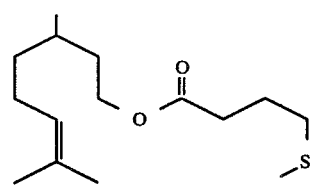

(with the mole ratio of the compound having the structure:

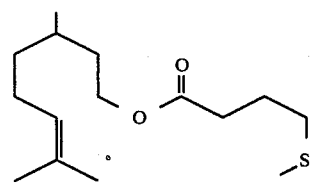

to compound having the structure:

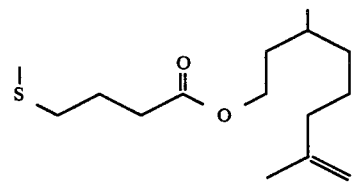

being 85:15).

FIG. 7 is the GLC profile for fraction 5 of the foregoing distillation containing a mixture of compounds having the structures:

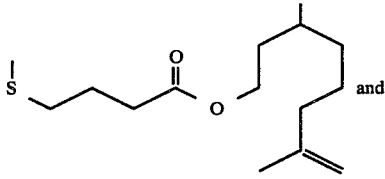 and

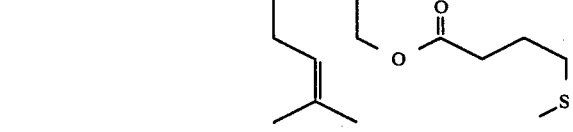

(with the mole ratio of the compound having the structure:

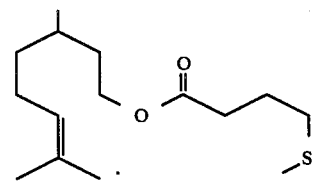

to compound having the structure:

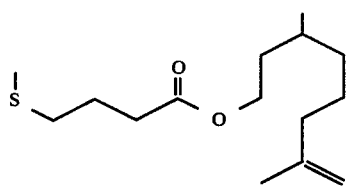

being 85:15).

FIG. 8 is the GLC profile for fraction 6 of the foregoing distillation containing a mixture of compounds having the structures:

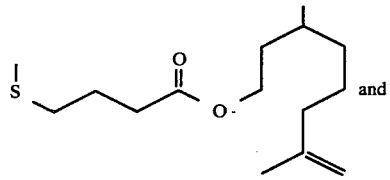

and

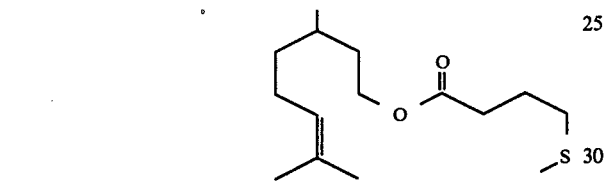

(with the mole ratio of the compound having the structure:

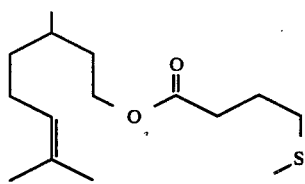

to compound having the structure:

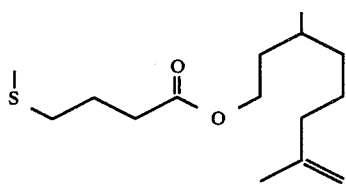

being 85:15).

FIG. 9 is the NMR spectrum for fraction 6 of the foregoing distillation containing a mixture of compounds having the structures:

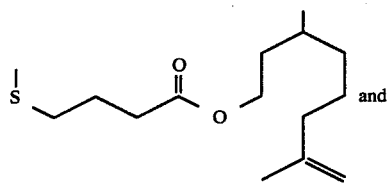

and

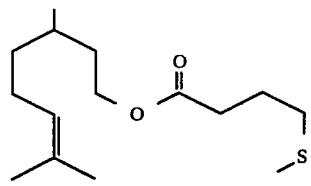

(with the mole ratio of the compound having the structure:

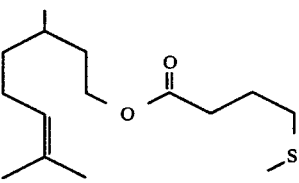

to compound having the structure:

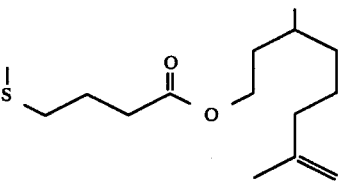

being 85:15) (Conditions: Field strength: 100 MHz; solvent: CFCl$_3$).

EXAMPLE III

The following two substances:
Substance "A":
The compound having the structure:

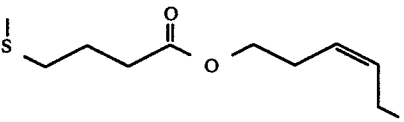

prepared according to Example I; and
Substance "B":
The mixture of compounds having the structures:

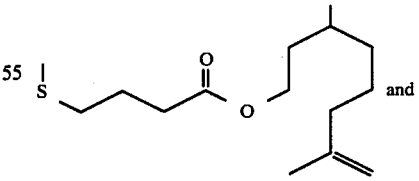

and

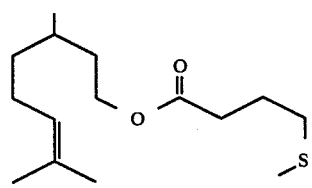

prepared according to Example II (mole ratio of compound having the structure:

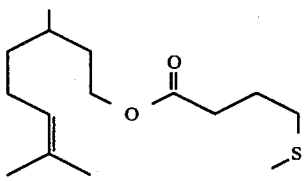

to compound having the structure:

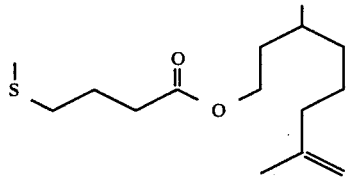

being 85:15)
are added separately at the rates of 2 ppm and 10 ppm to the following substances:

(i) GOYA ® Products Mango Nectar (manufactured by the Goya Foods Inc., Secaucus, N.J. 07094);
(ii) GOYA ® Guava Nectar (manufactured by the Goya Foods Inc., Secaucus, N.J. 07094)
(iii) GOYA ® Guava Paste (manufactured by the Goya Foods Inc., Secaucus, N.J. 07094); and
(iv) GOYA ® Products Papaya Nectar (manufactured by the Goya Foods Inc., Secaucus, N.J. 07094)

The addition of Substances "A" and "B" at the levels indicated, to the food products indicated, imparts to the food products a much more natural, ripe fruity flavor.

The compound having the structure:

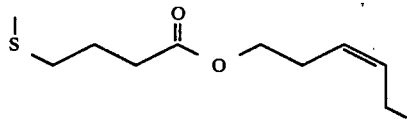

produced according to Example I imparts a green and spicy nuance to each of the above foods.

The mixture of compounds having the structures:

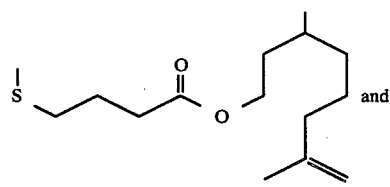

and

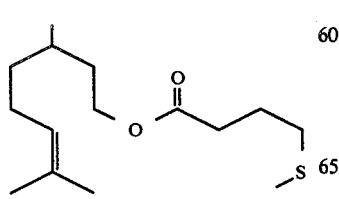

(mole ratio of compound having the structure:

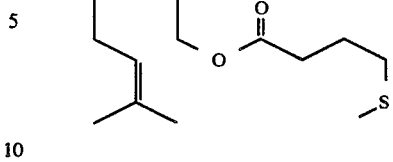

to compound having the structure:

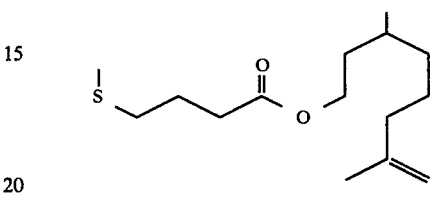

being 85:15) imparts fresh lemon, lemon juice-like and grapefruit nuances to the above-mentioned food substances.

A comparison was made between the methylthioalkanoic acid esters of cis-3-hexenol and citronellol of our invention and melonyl-4-(methylthio)butyrate having the structure:

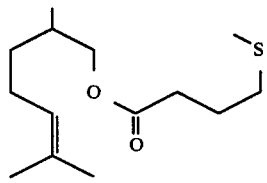

prepared according to the process:

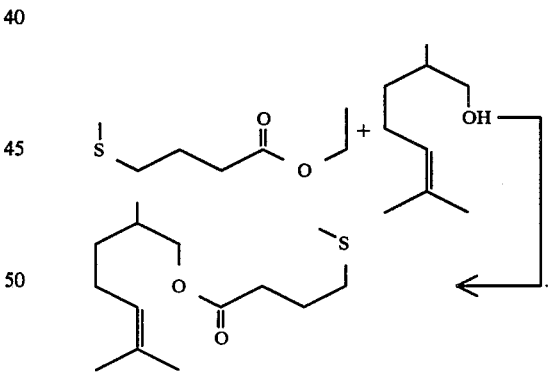

The compound having the structure:

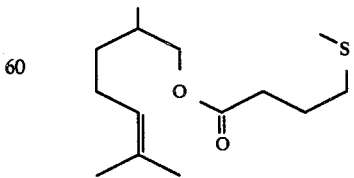

imparts to the above-mentioned food substances at levels of 2 ppm and 10 ppm melony and citronellol-like aroma and taste nuances.

The compound having the structure:

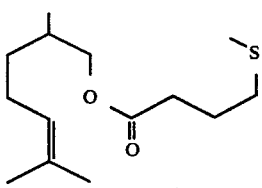

is not preferred as much as the compound having the structure:

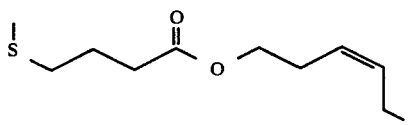

or the mixture of compounds having the structures:

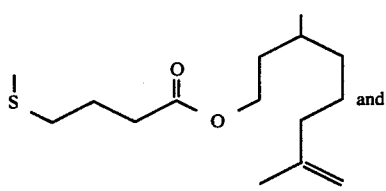

although the compound having the structure:

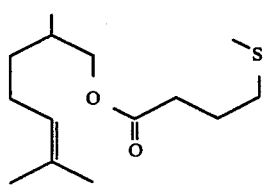

has some degree of use for augmenting or enhancing the aroma or taste of foodstuffs.

EXAMPLE IV

To GOYA® Guava Jelly (manufactured by the Goya Foods Inc., Secausus, N.J. 07094) containing:
Guava fruit;
Guava Juice;
Sugar;
Corn syrup;
Pectin; and
Citrus acid are placed at levels of 6 ppm and 12 ppm the following substances:

Substance "A": The compound having the structure:

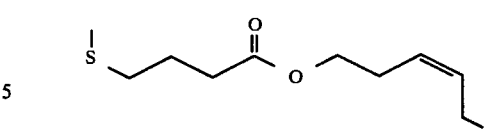

prepared according to Example I.

Substance "B": The mixture of compounds having the structures:

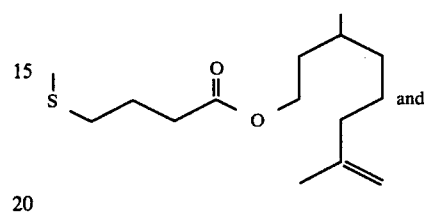

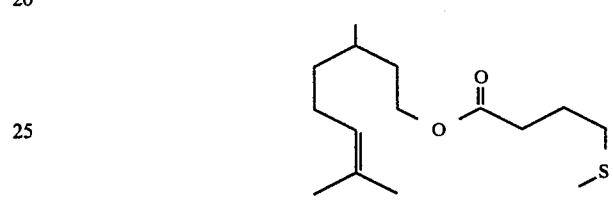

prepared according to Example II (mole ratio of compound having the structure:

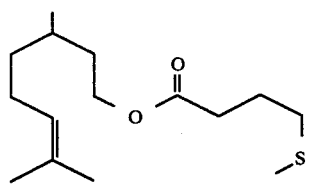

to compound having the structure:

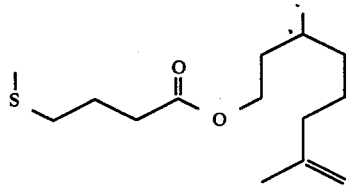

being 85:15).

Substance "C": The compound having the structure:

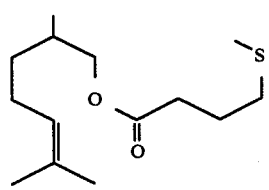

(the methylthiobutyrate of melanol)

In each of the cases, the resulting Guava jelly has excellent "ripe natural" citrusy nuances which render the jelly more aesthetically pleasing to a panel of five members. More specifically, the jelly containing Substance "A" has a "ripe natural tropical fruit flavor" with green, spicy and licorice nuances. The jelly containing Substance "B" has a Guava tropical fruit character with fresh lemon, lemon juice and grapefruit aroma and taste nuances. The jelly containing Substance "C" has a Guava taste with melony and citrusy aroma and taste nuances.

The panel of five members unanimously prefers the Guava jelly containing each of Substances "A", "B" and "C" to those jellies not containing any of Substances "A", "B" and "C". As between the Substances "A", "B" and "C", Substances "A" and "B" are preferred over Substance "C". The most preferred jelly is the one containing Substance "B".

What is claimed is:

1. A mixture of compounds having the structures:

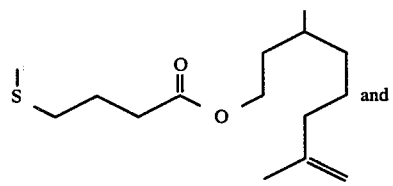 and

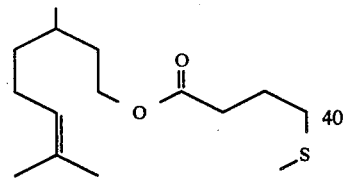

with the mole ratio of compound having the structure:

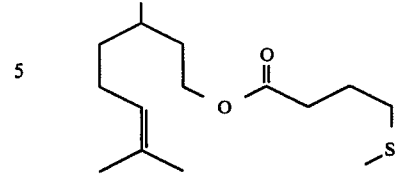

to compound having the structure:

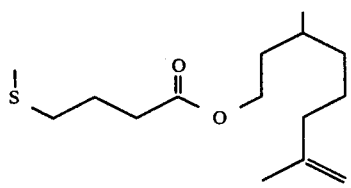

varying from about 70:30 up to about 90:10.

2. The mixture of claim 1 wherein the mole ratio of compound having the structure:

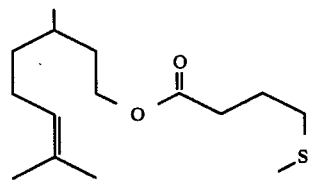

to compound having the structure:

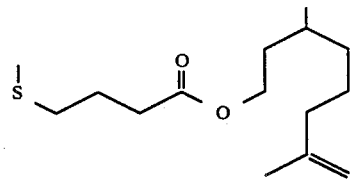

is 85:15.

* * * * *